United States Patent [19]

Attwood et al.

[11] Patent Number: 4,920,119
[45] Date of Patent: Apr. 24, 1990

[54] TRIAZINE DERIVATIVES

[75] Inventors: Michael R. Attwood, Hitchin; Peter H. Crackett, Baldock; Geoffrey Lawton, Hitchin, all of England

[73] Assignee: Hoffmann-La Roche Inc., Nutley, N.J.

[21] Appl. No.: 124,750

[22] Filed: Nov. 24, 1987

[30] Foreign Application Priority Data

Dec. 12, 1986 [GB] United Kingdom ............... 8629711
Sep. 14, 1987 [GB] United Kingdom ............... 8721564

[51] Int. Cl.⁵ .............. C07D 471/04; C07D 487/04; C07D 513/04; A61K 31/53
[52] U.S. Cl. .................... 514/243; 544/184
[58] Field of Search .................. 544/184; 514/243

[56] References Cited

U.S. PATENT DOCUMENTS

| | | | |
|---|---|---|---|
| 2,925,418 | 2/1960 | Druey et al. | 544/184 |
| 4,346,094 | 8/1982 | Beck et al. | 548/206 |
| 4,544,752 | 10/1985 | Beck et al. | 548/206 |
| 4,563,210 | 1/1986 | Beck et al. | 548/377 |

OTHER PUBLICATIONS

Stanovnik et al., Chemical Abstract, 88, (1978), 74365m.
C. Chen, Chemical Abstract, 68, (1968), 105170n.
C. Cheng, Chemical Abstract, 69, (1968), 67342f.
Hall et al., Chemical Abstract, 106, (1987), 46285g.
Long et al., Chemical Abstract, 73, (1970), 77193e.
P. Norton, Chemical Abstract, 106, (1987), 50103p.
Schneller et al., Chemical Abstract, 83, (1975), 10008m.
Beck, et al., J. Heterocyclic Chem., 1987, 24(1), pp. 243-5.
Schaefer, et al., J. Prakt. Chem. 1983, 325(1), pp. 41-8.
Schaefer, et al., Chem. Abst. 99:12236m, (1983).
Derwent 84-136034/22, (1984).

Primary Examiner—John M. Ford
Attorney, Agent, or Firm—George M. Gould; Bernard S. Leon; George W. Johnston

[57] ABSTRACT

Compounds of the formula

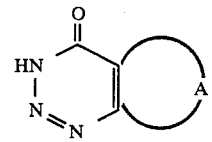

I wherein A represents a grouping of the formula

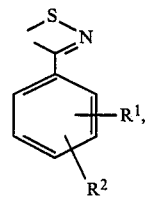

(a)

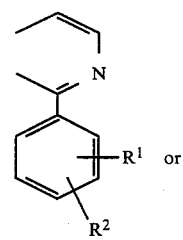

(b)

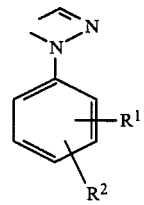

(c)

in which $R^1$ and $R^2$ each individually represent hydrogen, halogen, trifluoromethyl, nitro, amino, cyano, $C_1$–$C_6$-alkyl, $C_1$–$C_6$-alkoxy, $C_3$–$C_6$-alkenyloxy, $C_1$–$C_6$-alkylthio, $C_1$–$C_6$-alkanoylamino, aryloxy, aryl-($C_1$–$C_6$-alkyl), aryl-($C_1$–$C_6$-alkoxy), aryl-($C_1$–$C_6$-alkoxy)carbonylamino or a group of the formula —O—CH$_2$—$R^3$ or $R^1$ and $R^2$ on adjacent carbon atoms together represent a group of the formula —CH═CH—CH═CH— or —CH$_2$—CH$_2$—O— and $R^3$ represents hydroxy-($C_1$–$C_4$-alkyl) or vicinal dihydroxy-($C_2$–$C_5$-alkyl), and pharmaceutically acceptable acid addition salts of those compounds of formula I in which $R^1$ and/or $R^2$ represents amino, possess xanthine oxidase inhibiting activity and can be used as medicaments, particularly for the control or prevention of ischemia or gout. These compounds can be manufactured according to known methods.

17 Claims, No Drawings

TRIAZINE DERIVATIVES

BACKGROUND OF THE INVENTION

The present invention is concerned with triazine derivatives, a process for the manufacture thereof and medicaments containing said derivatives.

SUMMARY OF THE INVENTION

Triazine derivatives are provided by the present invention and have the formula

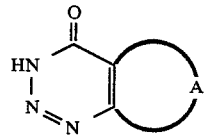

wherein A represents a grouping of the formula

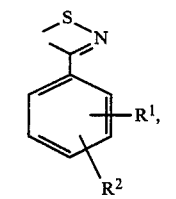

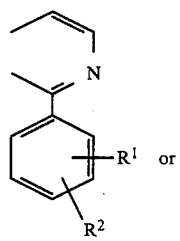

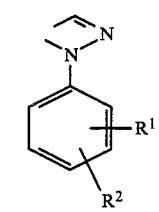

in which $R^1$ and $R^2$ each individually represent hydrogen halogen, trifluoromethyl, nitro, amino, cyano, $C_1$-$C_6$-alkyl, $C_1$-$C_6$-alkoxy, $C_3$-$C_6$-alkenyloxy, $C_1$-$C_6$-alkylthio, $C_1$-$C_6$-alkanoylamino, aryloxy, aryl-($C_1$-$C_6$-alkyl), aryl-($C_1$-$C_6$-alkoxy), aryl-($C_1$-$C_6$-alkoxy)carbonylamino or a group of the formula —O—CH$_2$—$R^3$ or $R^1$ and $R^2$ on adjacent carbon atoms together represent a group of the formula —CH=CH—CH=CH— or —CH$_2$—CH$_2$—O— and $R^3$ represents hydroxy-($C_1$-$C_4$-alkyl) or vicinal dihydroxy-($C_2$-$C_5$-alkyl), and pharmaceutically acceptable acid addition salts of those compounds of formula I in which $R^1$ and/or $R^2$ represents amino.

The compounds of formula I, per se, and pharmaceutically acceptable acid addition salts of such compounds in which $R^1$ and/or $R^2$ represents amino possess valuable pharmacodynamic properties. In particular, they inhibit xanthine oxidase and can be used in the control or prevention of ischemia which can be of myocardial cerebral renal and/or intestinal origin, or out.

DETAILED DESCRIPTION OF THE INVENTION

The triazine derivatives provided by the present invention are compounds of the formula

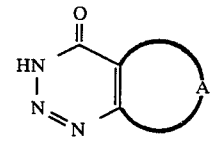

wherein A is a grouping of the formula

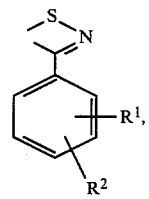

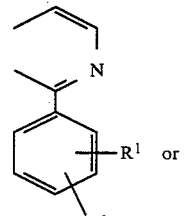

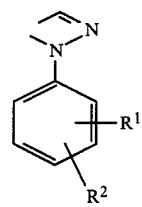

in which $R^1$ and $R^2$ each individually is hydrogen, halogen, trifluoromethyl, nitro, amino, cyano, $C_1$-$C_6$-alkyl, $C_1$-$C_6$-alkoxy, $C_3$-$C_6$-alkenyloxy, $C_1$-$C_6$-alkylthio, $C_1$-$C_6$-alkanoylamino, aryloxy, aryl-($C_1$-$C_6$-alkyl), aryl-($C_1$-$C_6$-alkoxy), aryl-($C_1$-$C_6$-alkoxy)carbonylamino or —O—CH$_2$—$R^3$, or $R^1$ and $R^2$ on adjacent carbon atoms together are —CH=CH—CH= CH— or —CH$_2$—CH$_2$—O—, and $R^3$ is hydroxy-($C_1$-$C_4$-alkyl) or vicinal dihydroxy-($C_2$-$C_5$-alkyl), and pharmaceutically acceptable acid addition salts of those compounds of formula I in which at least one of $R^1$ and $R^2$ is amino, or tautomers thereof.

As used herein, the terms "$C_1$-$C_4$-alkyl", "$C_2$-$C_5$-alkyl" and "$C_1$-$C_6$-alkyl", mean straight-chain or branched-chain alkyl groups which contain the number of carbon atoms specified, such as methyl, ethyl, n-propyl, isopropyl, n-butyl, sec.butyl, tert.butyl, n-pentyl, n-hexyl and the like. The term "$C_1$-$C_6$-alkoxy" means a $C_1$-$C_6$-alkyl group as defined above which is attached via an oxygen atom, examples of $C_1$-$C_6$-alkoxy groups being methoxy, ethoxy, n-propoxy, isopropoxy, n-butoxy, isobutoxy, tert.butoxy and the like. The term "$C_3$-$C_6$-alkenyloxy" means a straight-chain or branched-chain alkenyloxy group containing from 3 to 6 carbon atoms such as allyloxy, butenyloxy and the like. The term "$C_1$-$C_6$-alkylthio" means a $C_1$-$C_6$-alkyl group as defined above which is attached via a sulphur atom, examples of $C_1$-$C_6$-alkylthio groups being methylthio, ethylthio, n-propylthio, isopropylthio, n-butylthio and the like. The $C_1$-$C_6$-alkanoyl residue of a $C_1$-$C_6$-alkanoylamino group is derived from a straight-chain or branched-chain alkanecarboxylic acid containing from 1 to 6 carbon atoms such as formyl acetyl, propionyl, butyryl and the like. The aryl moiety of an aryloxy, aryl-($C_1$-$C_6$-alkyl), aryl-($C_1$-$C_6$-alkoxy) or aryl-($C_1$-$C_6$-alkoxy)carbonylamino group is an unsubstituted phenyl group or a phenyl group carrying at least one substituent selected from halogen, trifluoromethyl. $C_1$-$C_6$-alkyl, $C_1$-$C_6$-alkoxy, nitro and cyano. Phenoxy, 4-chlorophenoxy, 4-tolyloxy etc are examples of aryloxy groups. Benzyl, 4-chlorobenzyl, 4-tolyl, 4-methoxybenzyl, phenethyl etc are examples of aryl-($C_1$-$C_6$-alkyl) groups. Benzyloxy, 4-chlorobenzyloxy, 4-tolyloxy, 4-methoxybenzyloxy etc are examples of aryl-($C_1$-$C_6$-alkoxy) groups. Examples of groups of the formula —O—$CH_2$—$R^3$ are 2-hydroxyethoxy, 3-hydroxypropoxy and the like when $R^3$ represents hydroxy-($C_1$-$C_4$-alkyl) and 2,3-dihydroxypropoxy, 3,4-dihydroxybutoxy and the like when $R^3$ represents vicinal dihydroxy-($C_2$-$C_5$-alkyl). The term "halogen" means fluorine, chlorine, bromine or iodine.

The compounds of formula I in which $R^1$ and/or $R^2$ represents amino form pharmaceutically acceptable salts with acids. Examples of such salts are mineral acid salts such as hydrohalides (e.g. hydrochlorides, hydrobromides etc), sulphates, phosphates, nitrates etc and organic acid salts such as acetates, maleates, fumarates, tartrates, citrates, salicylates, methanesulphonates, p-toluenesulphonates etc.

It will be appreciated that the compounds of formula I can exist in tautomeric forms of the formulae

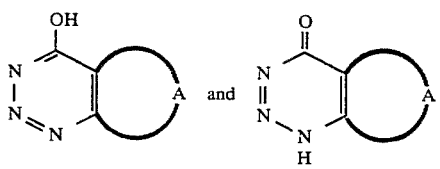

wherein A has the significance given earlier, and that such tautomers also form part of the present invention.

One preferred class of compounds of formula I above comprises those in which A represents a group of formula (a). In such compounds $R^1$ preferably represents hydrogen, halogen, trifluoromethyl or cyano and $R^2$ preferably represents hydrogen $C_1$-$C_6$-alkoxy, aryl-($C_1$-$C_6$-alkoxy) or a group of the formula —O—$CH_2$—$R^3$ in which $R^3$ represents vicinal dihydroxy-($C_2$-$C_5$-alkyl), with the proviso that at least one of $R^1$ and $R^2$ represents other than hydrogen.

The most preferred compounds of formula I in which A represents a group of formula (a) are:

7-(3-Trifluoromethyl-4-methoxyphenyl)isothiazolo[4,5-d]-1,2,3-triazin-4(3H)-one,
7-(3-chloro-4-methoxyphenyl)isothiazolo[4,5-d]-1,2,3-triazin-4(3H)-one,
7-(3-fluoro-4-methoxyphenyl)isothiazolo[4,5-d]-1,2,3-triazin-4(3H)-one,
7-(3-trifluoromethylphenyl)isothiazolo[4,5-d]-1,2,3-triazin-4(3H)-one,
7-(4-isopropoxyphenyl)isothiazolo[4,5-d]-1,2,3-triazin-4(3H)-one,
7-(4-benzyloxyphenyl)isothiazolo[4,5-d]-1,2,3-triazin-4(3H)-one,
7-(3-cyano-4-methoxyphenyl)isothiazolo[4,5-d]-1,2,3-triazin-4(3H)-one and
7-[3-cyano-4-(2,3-dihydroxypropoxy)phenyl)isothiazolo[4,5-d]-1,2,3-triazin-4(3H)-ene.

Another preferred class of compounds of formula I comprises those in which A represents a group of formula (c). In such compounds R preferably represents hydrogen and $R^2$ preferably represents $C_1$-$C_6$-alkoxy.

The most preferred compound of formula I in which A represents a group of formula (c) is 7-(4-methoxyphenyl)-7H-pyrazolo[3,4-d]-1,2,3-triazin-4(3H)-one.

Examples of other interesting compounds of formula I are:

7-Phenylisothiazolo[4,5-d)-1,2,3-triazin-4(3H)-one,
7-(3-ethylphenyl)isothiazolo[4,5-d]-1,2,3-triazin-4(3H)-one,
7-(3-methylphenyl)isothiazolo[4,5-d]-1,2,3-triazin-4(3H)-one,
7-(3-chlorophenyl)isothiazolo[4,5-d]-1,2,3-triazin-4(3H)-one,
7-(3-bromophenyl)isothiazolo[4,5-d]-1,2,3-triazin-4(3H)-one,
7-(3-cyanophenyl)isothiazolo[4,5-d]-1,2,3-triazin-4(3H)-one,
7-(3-methoxyphenyl)isothiazolo[4,5-d]-1,2,3-triazin-4(3H)-one,
7-(4-methoxyphenyl)isothiazolo[4,5-d]-1,2,3-triazin-4(3H)-one,
7-(3-fluorophenyl)isothiazolo[4,5-d]-1,2,3-triazin-4(3H)-one,
7-(4-acetamidophenyl)isothiazolo[4,5-d]-1,2,3-triazin-4(3H)-one,
7-(4-benzyloxyformamidophenyl)isothiazolo[4,5-d]-1,2,3-triazin-4(3H)-one,
7-(4-aminophenyl)isothiazolo[4,5-d]-1,2,3-triazin-4(3H)-one,
7-(4-nitrophenyl)isothiazolo[4,5-d]-1,2,3-triazin-4(3H)-one,
7-(4-chlorophenyl)isothiazolo[4,5-d]-1,2,3-triazin-4(3H)-one,
7-(4-bromophenyl)isothiazolo[4,5-d]-1,2,3-triazin-4(3H)-one,
7-(4-phenoxyphenyl)isothiazolo[4,5-d]-1,2,3-triazin-4(3H)-one,
7-(2-naphthyl)isothiazolo[4,5-d]-1,2,3-triazin-4(3H)-one,
7-(2,3-dihydro-5-benzofuranyl)isothiazolo[4,5-d]-1,2,3-triazin-4(3H)-one,
7-(3,5-dimethylphenyl)isothiazolo[4,5-d]-1,2,3-triazin-4(3H)-one,
7-(4-benzylphenyl)isothiazolo[4,5-d]-1,2,3-triazin-4(3H)-one,
7-(3-isopropylphenyl)isothiazolo[4,5-d]-1,2,3-triazin-4(3H)-one,
7-[3,5-bis(trifluoromethyl)phenyl]isothiazolo[4,5-d]-1,2,3-triazin-4(3H)-one,
7-(3-trifluoromethyl-4-benzyloxyphenyl)isothiazolo[4,5-d]-1,2,3-triazin-4(3H)-one,
8-phenylpyrido[3,4-d]-1,2,3-triazin-4(3H)-one,
8-(3-trifluoromethylphenyl)pyrido[3,4-d]-1,2,3-triazin-4(3H)-one,
7-phenyl-7H-pyrazolo[3,4-d]-1,2,3-triazin-4(3H)-one, 7-(3-trifluoromethylphenyl)-7H-pyrazolo[3,4-d]-1,2,3-triazin-4(3H)-one, 7-(3-chlorophenyl)-7H-pyrazolo[3,4-d]-1,2,3-triazin-4(3H)-one, 7-(4-ethylphenyl)-7H-pyrazolo[3,4-d]-1,2,3-triazin-4(3H)-one, 7-(4-methylthiophenyl)-7H-pyrazolo[3,4-d]-1,2,3-triazin-4(3H)-one and 7-(3-chloro-4-methoxyphenyl)-7H-pyrazolo[3,4-d]-1,2,3-triazin-4(3H)-one.

Further interesting compounds of formula I are:

7-(4-Ethylphenyl)isothiazolo[4,5-d]-1,2,3-triazin-4(3H)-one, 7-(4-isobutylphenyl)isothiazolo[4,5-d]-1,2,3-triazin-4(3H)-one, 7-(4-allyloxy-3-cyanophenyl)isothiazolo[4,5-d]-1,2,3-triazin-4(3H)-one, 7-[3-cyano-4-(2-hydroxyethoxy)phenyl]isothiazolo[4,5-d]-1,2,3-triazin-4(3H)-one, 7-[3-cyano-4-(3-hydroxypropoxy)phenyl]isothiazolo[4,5-d]-1,2,3-triazin-4(3H)-one, 7-(3-cyano-4-methylthiophenyl)isothiazolo[4,5-d]-1,2,3-triazin-4(3H)-one, 8-(4-methoxyphenyl)pyrido[3,4-d]-1,2,3-triazin-4(3H)-one, 8-(4-benzyloxyphenyl)pyrido[3,4-d]-1,2,3-triazin-4(3H)-one, 8-(3-fluoro-4-methoxyphenyl)pyrido[3,4-d]-1,2,3-triazin-4(3H)-one, 8-(3-chloro-4-methoxyphenyl)pyrido[3,4-d]-1,2,3-triazin-4(3H)-one, 8-(4-methoxy-3-trifluoromethylphenyl)pyrido[3,4-d]-1,2,3-triazin-4(3H)-one and 8-(4-benzyloxy-3-trifluoromethylphenyl)pyrido[3,4-d]-1,2,3-triazin-4(3H)-one.

According to the process provided by the present invention, the compounds of formula I above and pharmaceutically acceptable salts of those compounds of formula I in which R and/or R represents amino are manufactured as follows:

(a) for the manufacture of a compound of formula I in which $R^1$ and $R^2$ each individually represent hydrogen halogen, trifluoromethyl, nitro, cyano, $C_1$–$C_6$-alkyl, $C_1$–$C_6$-alkoxy, $C_3$–$C_6$-alkenyloxy, $C_1$–$C_6$-alkylthio, $C_1$–$C_6$-alkanoylamino, aryloxy, aryl-($C_1$–$C_6$-alkyl), aryl-($C_1$–$C_6$-alkoxy), aryl-($C_1$–$C_6$-alkoxy)carbonylamino carbonylamino or a group of the formula —O—$CH_2$—$R^3$ or $R^1$ and $R^2$ on adjacent carbon atoms together represent a group of the formula —CH=CH—CH=CH— or —$CH_2$—$CH_2$—O— and $R^3$ represents hydroxy-($C_1$–$C_4$-alkyl), reacting a compound of the general formula

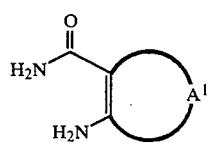

II wherein $R^1$ represents a grouping of the formula

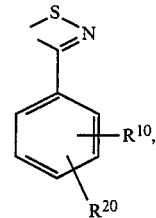

(a')

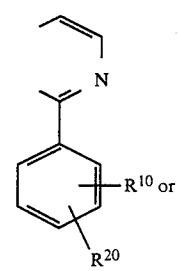

(b')

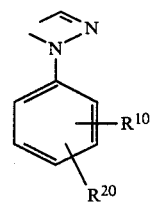

(c')

in which and each individually represent hydrogen, halogen, trifluoromethyl, nitro, cyano, $C_1$–$C_6$-alkyl, $C_1$–$C_6$-alkoxy, $C_3$–$C_6$-alkenyloxy, $C_1$–$C_6$-alkylthio, $C_1$–$C_6$-alkanoylamino, aryloxy, aryl-($C_1$–$C_6$-alkyl), aryl-($C_1$–$C_6$-alkoxy), aryl-($C_1$–$C_6$-alkoxy)carbonylamino or a group of the formula —O—$CH_2$—$R^{30}$ or $R^{10}$ and $R^{20}$ agent carbon atoms together represent a group of the formula —CH=CH—CH=CH— or —$CH_2$—$CH_2$—O— and $R^{30}$ represents hydroxy-($C_1$–$C_4$-alkyl), with nitrous acid, or (b) for the manufacture of a compound of formula I in which $R^1$ and/or $R^2$ represents amino, cleaving the aryl-($C_1$–$C_6$-alkoxy)carbonylamino group(s) in a compound of formula I in which $R^1$ and/or $R^2$ represents aryl-($C_1$–$C_6$-alkoxy)carbonylamino, or (c) for the manufacture of a compound of formula I in which $R^1$ and/or $R^2$ represents $C_1$–$C_6$-alkanoylamino, appropriately acylating a compound of formula I in which $R^1$ and/or $R^2$ represents amino, or (d) for the manufacture of a compound of formula I in which $R^1$ and/or $R^2$ represents a group of the formula —O—$CH_2$—$R^3$ in which $R^3$ represents hydroxy-($C_1$–$C_4$-alkyl), reacting a compound of formula I in which $R^1$ and/or $R^2$ represents $C_3$–$C_6$-alkenyloxy with ozone and reducing the reaction product with a complex metal hydride, or (e) for the manufacture of a compound of formula I in which $R^1$ and/or $R^2$ represents a group of the formula —O—$CH_2$—$R^3$ in which $R^3$ represents vicinal dihydroxy-($C_2$–$C_5$-alkyl), reacting a compound of formula I in which $R^1$ and/or $R^2$ represents $C_3$–$C_6$-alkenyloxy with osmium tetroxide and (f) if desired, converting a compound of formula I obtained in which $R^1$ and/or $R^2$ represents amino into a pharmaceutically acceptable acid addition salt.

The reaction of a compound of formula II with nitrous acid in accordance with embodiment (a) of the process can be carried out in a known manner. Thus, for example, a compound of formula II can be treated with a strong inorganic acid, suitably a hydrohalic acid such as hydrochloric acid, and an alkali metal nitrite, suitably sodium nitrite, in an aqueous medium at a low temperature (e.g. about 0° C.). whereby the nitrous acid is generated in situ. If desired, the aqueous medium can contain an inert water-miscible organic solvent such as a $C_2$-$C_6$-alkanecarboxylic acid (e.g. acetic acid), a $C_1$-$C_6$-alkanol (e.g. ethanol), N,N-dimethylformamide dimethyl sulphoxide, N-methylpyrrolidone or the like. Alternatively, a compound of formula II can he heated, preferably at the reflux temperature, with isoamyl nitrite in the presence of an inert organic solvent which is not miscible with water, for example a halogenated hydrocarbon such as chloroform.

The cleavage of the aryl-(lower alkoxy)carbonylamino group(s), preferably benzyloxycarbonylamino group(s), in accordance with embodiment (b) of the process can also be carried out in a known manner. Preferably, the cleavage is carried out by treatment with an acid, suitably a halogenated $C_2$–$C_6$-alkanecarboxylic acid, preferably trifluoroacetic acid, expediently at an elevated temperature (e.g. at the reflux temperature), although any other appropriate acid (e.g. hydrogen bromide in glacial acetic acid or hydrogen chloride in ethyl acetate) can also be used. The cleavage can also be carried out by hydrogenation in the presence of a suitable catalyst such as palladium-on-charcoal, conveniently in an inert orqanic solvent such as a $C_1$–$C_6$ alkanol (e.g. methanol, ethanol etc) at about room temperature and under atmospheric pressure. However, the cleavage by catalytic hydrogenation is not preferred when A in the compound of formula I represents a grouping of formula (a).

The acylation of a compound of formula I in which $R^1$ and/or $R^2$ represents amino in accordance with embodiment (c) of the process can also be carried out in a known manner. Conveniently, the acylation is carried out using an appropriate alkanecarboxylic anhydride such as acetic anhydride, expediently at an elevated temperature (e.g. at about 100° C.). However, the acylation can also be carried out using other reactive derivatives of appropriate alkanecarboxylic acids, for example alkanecarboxylic acid halides such as chlorides, in accordance with known methods.

The reaction of a compound of formula I in which $R^1$ and/or $R^2$ represents $C_3$-$C_6$-alkenyloxy with ozone and the reduction of the reaction product with a complex metal hydride in accordance with embodiment (d) of the process can be carried out according to methods known per se. For example, the reaction with ozone can he suitably carried out by passing ozone through a solution of the starting material of formula I in an inert organic solvent such as a $C_1$-$C_6$-alkanol (e.g. methanol, ethanol etc), a cyclic ether (e.g. tetrahydrofuran etc) or a mixture thereof, conveniently at about room temperature. The reaction product, conveniently without isolation is then reduced with a complex metal hydride such as an alkali metal borohydride (e.g. sodium borohydride), lithium aluminium hydride diisobutylaluminium hydride or the like suitably at about room temperature.

Methods known per se can also be used for the reaction of a compound of formula I in which $R^1$ and/or $R^2$ represents $C_3$-$C_6$-alkenyloxy with osmium tetroxide in accordance with embodiment (e) of the process. Thus, the reaction with osmium tetroxide can be carried out conveniently in a mixture of water and an inert organic solvent which is miscible with water (e.g. dimethylformamide), conveniently at about room temperature. If desired, the reaction can be carried out in the presence of a reagent such as N-methylmorpholine N-oxide which oxidizes the osmium derivatives formed during the reaction to osmium tetroxide. After the reaction, the reaction mixture is conveniently treated with an alkali metal dithionite, preferably sodium dithionite, suitably in the form of an aqueous solution and expediently at about room temperature, in order to reduce the osmium salts present to a form in which they can be readily separated from the desired compound of formula I.

The conversion of a compound of formula I in which $R^1$ and/or $R^2$ represents amino into a pharmaceutically acceptable acid addition salt in accordance with embodiment (f) of the process can be carried out in a known manner. Thus, such a compound of formula I can he converted into a pharmaceutically acceptable acid addition salt by treatment with a mineral acid (e.g. a hydrohalic acid such as hydrochloric acid, hydrobromic acid etc, sulphuric acid, nitric acid, phosphoric acid etc) or an orqanic acid (e.g. acetic acid, maleic acid, fumaric acid, tartaric acid, citric acid, salicylic acid, methanesulphonic acid, p-toluenesulphonic acid etc).

The compounds of formula II which are used as starting materials are known compounds or analogues of known compounds which can be prepared in a similar manner to the known compounds. Further, certain of the Examples hereinafter contain detailed information concerning the preparation of the respective starting materials.

The compounds of formula I and pharmaceutically acceptable acid addition salts of such compounds in which $R^1$ and/or $R^2$ represents amino possess valuable pharmacodynamic properties. In particular, they inhibit xanthine oxidase and can be used in the control or prevention of ischemia, which can be of myocardial, cerebral, renal and/or intestinal origin or gout.

The xanthine oxidase inhibiting activity of the present compounds can be demonstrated in the following test.

Xanthine oxidase was obtained from rat liver according to the method described by E. Della Corte and F. Stirpe in Biochem.J. 117, 97 (1970) and was aged for at least 24 hours prior to use. Solutions of 3 ml of 0.1M aqueous tris hydrochloride buffer (pH 8.1) containing $10^{-5}$ molar xanthine were treated with 200 $\mu$l of xanthine oxidase dissolved in 0.1M aqueous tris hydrochloride buffer (pH 8.1) and incubated at 30° C. in the presence and absence of a test substance, whereupon the formation of uric acid from xanthine was monitored by measuring the light absorption at 293 nm. The $IC_{50}$, namely that concentration of a test substance required to inhibit by 50% the xanthine oxidase-catalyzed oxidation of xanthine to uric acid, was then determined.

The results obtained in the foregoing test using representative compounds of formula I as test substances are given in the following Table.

TABLE

| Compound of formula I | $IC_{50}$ (nmol) |
|---|---|
| 7-(3-Trifluoromethyl-4-methoxyphenyl)-isothiazolo[4,5-d]-1,2,3-triazin-4(3H)-one | 4 |
| 7-(3-Chloro-4-methoxyphenyl)isothiazolo-[4,5-d]-1,2,3-triazin-4(3H)-one | 4 |
| 7-(3-Fluoro-4-methoxyphenyl)isothiazolo-[4,5-d]-1,2,3-triazin-4(3H)-one | 8 |
| 7-(4-Acetamidophenyl)isothiazolo[4,5-d]-1,2,3-triazin-4(3H)-one | 7 |

TABLE-continued

| Compound of formula I | IC$_{50}$ (nmol) |
| --- | --- |
| 8-(3-Trifluoromethylphenyl)pyrido[3,4-d]-1,2,3-triazin-4(3H)-one | 48 |
| 7-(3-Chloro-4-methoxyphenyl)-7H-pyrazolo-[3,4-d]-1,2,3-triazin-4(3H)-one | 6 |
| 7-(4-Methylthiophenyl)-7H-pyrazolo[3,4-d]-1,2,3-triazin-4(3H)-one | 18 |
| 7-(3-Trifluoromethylphenyl)-7H-pyrazolo-[3,4-d]-1,2,3-triazin-4(3H)-one | 35 |

The compounds of formula 1 and pharmaceutically acceptable acid addition salts of such compounds in which R$^1$ and/or R$^2$ represents amino can be used as medicaments, for example in the form of pharmaceutical preparations. The pharmaceutical preparations can be administered orally, for example in the form of tablets, coated tablets, dragees, hard and soft gelatine capsules, solutions, emulsions or suspensions. They can, however, also be administered rectally, for example in the form of suppositories, or parenterally, for example in the form of injection solutions.

For the manufacture of pharmaceutical preparations the compounds of formula I and pharmaceutically acceptable acid addition salts of such compounds in which R$^1$ and/or R$^2$ represents amino can be processed with pharmaceutically inert inorganic or organic excipients. Suitable excipients which can be used for tablets, coated tablets, dragees and hard gelatine capsule are, for example, lactose, maize starch or derivatives thereof, talc, stearic acid or its salts etc. Suitable excipients for soft gelatine capsules are, for example, vegetable oils, waxes, fats, semi-solid and liquid polyols etc. Water, polyols, saccharose, invert sugar, glucose etc are examples of suitable excipients for the manufacture of solutions and syrups. Suitable excipients for injection solutions are, for example, water, alcohols, polyols, glycerine, vegetable oils etc. Natural or hardened oils, waxes, fats, semi-liquid or liquid polyols etc are examples of suitable excipients for suppositories.

The pharmaceutical preparations can also contain preserving agents, solubilizing agents, stabilizing agents, wetting agents, emulsifying agents, sweetening agents, colouring agents, flavoring agents, salt for varying the osmotic pressure, buffers, coating agents or antioxidants. They can also contain other therapeutically valuable substances.

Moreover, the pharmaceutical composition for administering to patients preferably contains about 2% to about 50% by weight of the compound of formula I and its acid addition salt wherein R$^1$ and/or R$^2$ represent(s) amino and 50% to 98% by weight of a pharmaceutically acceptable carrier material, the composition preferably being formulated into a unit dosage form.

In accordance with the invention the compounds of formula I and pharmaceutically acceptable salts of such compounds in which R$^1$ and/or R$^2$ represent(s) amino can be used in the control or prevention of illnesses, especially of ischemia or gout. The dosage of the compounds of formula I can vary within wide limits and will, of course, be adjusted to the individual requirements in each particular case. In general, in the case of oral administration to adults, a daily dosage of about 5 mg to about 500 mg should be appropriate, although the upper limit mentioned can be exceeded when this is shown to be expedient. The daily dosage can be administered as a single dosage or in divided doses.

The following Examples illustrate the present invention. Unless otherwise stated, percentages and ratios are expressed in volume. Temperatures are in degrees Celsius (°C.). normal pressure is about 1 atmosphere and room temperature is about 23 ° C. The petroleum ether is a well-known mixture of low-boiling hydrocarbons. Unless, indicated otherwise, the Examples were carried out as written.

EXAMPLE 1

219 mg of 4-amino-3-phenyl-5-isothiazolecarboxamide in 7.2 ml of glacial acetic acid and 4 ml of concentrated hydrochloric acid were stirred at 0° C. during the addition of a solution of 80 mg of sodium nitrite in 1.2 ml of water. The mixture was held at below room temperature overnight and the precipitated product was filtered off and recrystallized from methanol to give 164 mg of 7-phenylisothiazolo[4,5-d]-1,2,3-triazin-4(3H)-one. A sample recrystallized from aqueous methanol melted at 179°-180° C. (dec.).

EXAMPLE 2

496 mg of 4-amino-3-(3-ethylphenyl)-5-isothiazolecarboxamide in 7 ml of glacial acetic acid, 4 ml of concentrated hydrochloric acid and 4 ml of N-methyl-pyrrolidone was stirred at 0° C. during the addition of 165 mg of sodium nitrite in 1 ml of water. The mixture was held at 0° C. for 1.5 hours then filtered and the solid residue was recrystallized from ethanol to give 400 mg of 7-(3-ethylphenyl)isothiazolo[4,5-d]-1,2,3-triazin-4(3H)-one, m.p. 156°-157° C. (dec.).

EXAMPLE 3

1 g of 4-amino-3-(4-methoxyphenyl)-5-isothiazolecarboxamide in 10 ml of glacial acetic acid and 3 ml of concentrated hydrochloric acid was stirred at 0° C. during the addition of a solution of 416 mg of sodium nitrite in 5 ml of water. The cooling bath was removed, the mixture was stirred for 1 hour and the precipitated product was removed by filtration. Recrystallization from aqueous dimethylformamide gave 820 mg of 7-(4-methoxyphenyl)-isothiazolo[4,5-d]-1,2,3-triazin-4(3H)-one as an off-white solid of melting point 213° C. (dec.).

EXAMPLE 4

The following compounds were prepared in a manner analogous to that described in Examples 1–3:
7-(3-Methylphenyl)isothiazolo[4,5-d]-1,2,3-triazin-4(3H)-one, m.p. 181°-183° C. (dec.);
7-(3-chlorophenyl)isothiazolo[4,5-d]-1,2,3-triazin-4(3H)-one, m.p. 190° C. (dec.);
7-(3-bromophenyl)isothiazolo[4,5-d]-1,2,3-triazin-4(3H)-one, m.p. 184°-185° C. (dec.);
7-(3-cyanophenyl)isothiazolo[4,5-d]-1,2,3-triazin-4(3H)-one, m.p. 190° C. (dec.);
7-(3-methoxyphenyl)isothiazolo[4,5-d]-1,2,3-triazin-4(3H)-one, m.p. 189°-190° C.;
7-(3-fluorophenyl)isothiazolo[4,5-d]-1,2,3-triazin-4(3H)-one, m.p. 183° C. (dec.);
7-(3-trifluoromethylphenyl)isothiazolo[4,5-d]-1,2,3-triazin-4(3H)-one, m.p. 215°-216° C. (dec.);
7-(4-isopropoxyphenyl)isothiazolo[4,5-d]-1,2,3-triazin-4(3H)-one, m.p. 187° C. (dec.);
7-(4-benzyloxyphenyl)isothiazolo[4,5-d]-1,2,3-triazin-4(3H)-one, m.p. 197° C. (dec.);
7-(4-nitrophenyl)isothlazolo[4,5-d]-1,2,3-trlazin-4(3H)-one, m.p. 201°-204° C. (dec.);

7-(4-chlorophenyl)isothiazolo[4 5-d]-1,2,3-triazin-4(3H)-one, m.p. 191° C. (dec.);
7-(4-bromophenyl)isothiazolo[4 5-d]-1,2,3-triazin-4(3H)-one, m.p 207° C. (dec.);
7-(4-phenoxyphenyl)isothiazolo[4,5-d]-1,2,3-triazin-4(3H)-one, m.p. 170° C. (dec.);
7-(2-naphthyl)isothiazolo[4,5-d]-1,2,3-triazin-4(3H)-one, m p. 189° C. (dec.);
7-(2,3-dihydro-5-benzofuranyl)isothiazolo[4,5-d]-1,2,3-triazin-4(3H)-one, m.p. 209° C. (dec.);
7-(3-fluoro-4-methoxyphenyl)isothiazolo[4,5-d]-1,2,3-triazin-4(3H)-one, m.p. 198°-199° C. (dec.):
7-(3-chloro-4-methoxyphenyl)isothiazolo[4,5-d]-1,2,3-triazin-4(3H)-one, m.p. 210° C. (dec.);
7-(3-trifluoromethyl-4-methoxyphenyl)isothiazolo[4,5-d]-1,2,3-triazin-4(3H)-one, m.p. 232° C. (dec.).
7-(3,5-dimethylphenyl)isothiazolo[4,5-d]-1,2,3-triazin-4(3H)-one, m.p. 188° C. (dec.);
7-(4-benzylphenyl)isothiazolo[4,5-d]-1,2,3-triazin-4(3H)-one, m.p. 174°-175° C. (dec.);
7-(3-isopropylphenyl)isothiazolo[4,5-d]-1,2,3-triazin-4(3H)-one, m.p. 155°-156° C. (dec.);
7-[3,5-bis(trifluoromethyl)phenyl]isothiazolo[4,5-d]-2,3-triazin-4-(3H)-one, m.p. 240°-242° C. (dec.);
7-(3-trifluoromethyl-4-benzyloxyphenyl)isothiazolo[4,5-d]-1,2,3-triazin-4(3H)-one, m.p. 199° C. (dec.);
7-(4-ethylphenyl)isothiazolo[4,5-d]-1,2,3-triazin-4(3H)-one, m.p. 172°-173° C. (dec.);
7-(4-isobutylphenyl)isothiazolo[4,5-d]-1,2,3-triazin-one, m.p. 178° C. (dec.);
7-(3-cyano-4-methoxyphenyl)isothiazolo[4,5-d]-1,2,3-triazin-4(3H)-one, m.p. 216°-219° C. (dec.);
7-(4-allyloxy-3-cyanophenyl)isothiazolo[4,5-d]-1,2,3-triazin-4(3H)-one, m.p. 185°-187° C. (dec.);
7-[3-cyano-4-(3-hydroxypropoxy)phenyl]isothiazolo[4,5-d]-1,2,3-triazin-4(3H)-one, m.p. 194°-197° C. (dec): and
7-[3-cyano-4-methylthiephenyl)isothiazolo[4,5-d]-1,2,3-triazin-4(3H)-one, m.p. 204°-205° C. (dec).

EXAMPLE 5

22.5 g of 4-amino-3-(4-benzyloxyformamidophenyl)-5-isothiazolecarboxamide in 25 ml of concentrated hydrochloric acid and 150 ml of N-methylpyrrolidone were cooled in an ice-bath and stirred during the addition of 4.89 g of sodium nitrite dissolved in 20 ml of water. After 0.5 hour 150 ml of water were added and the resulting precipitate was filtered off, washed with water, dried in vacuo and recrystallized from ethyl acetate to yield 16.6 g of 7-(4-benzyloxyformamidophenyl)isothiazolo[4,5-d]-1,2,3-triazin-4(3H)-one of melting point 190°-191° C. (dec.).

EXAMPLE 6

1 g of 7-(4-benzyloxyformamidophenyl)isothiazolo[4,5-d]-1,2,3-triazin-4(3H)-one in 10 ml of trifluoroacetic acid was heated under reflux for 1 hour. The solution was evaporated and the residue was partitioned between ethyl acetate and aqueous sodium carbonate solution. The aqueous layer was acidified with acetic acid and the precipitate which formed was extracted into hot ethyl acetate. The organic extract was dried over sodium sulphate and evaporated. The residue was chromatographed over silica gel using ethyl acetate/petroleum ether (2:1) for the elution. The product was crystallized from ethanol, then redissolved in 30 ml of ethanol and treated with 2 ml of concentrated hydrochloric acid to precipitate 7-(4-aminophenyl)isothiazolo[4 5-d]-1,2,3-triazin-4(3H)-one hydrochloride of melting point >280° C.

EXAMPLE 7

71 mg of 7-(4-aminophenyl)isothiazolo[4,5-d]-1,2,3-triazin-4(3H)-one hydrochloride were partitioned between ethyl acetate and aqueous sodium bicarbonate solution. The organic phase was dried over sodium sulphate and evaporated. The residue was treated with 5 ml of acetic anhydride at 100° C. until a clear solution was obtained. Excess acetic anhydride was removed by evaporation and the residue was chromatographed on silica gel using firstly ethyl acetate and then ethyl acetate/methanol (19:1) for the elution. The product was recrystallized from acetic acid to yield 7-(4-acetamidophenyl)isothiazolo[4 5-d]-1,2,3-triazin-4(3H)-one of melting point 239° C. (dec.).

EXAMPLE 8

Ozone was bubbled through a solution of 50 mg of 7-(4-allyloxy-3-cyanophenyl)isothiazolo[4,5-d]-1,2,3-triazin-4(3H)-one in 10 ml of ethanol and 2 ml of tetrahydrofuran for 20 minutes. Nitrogen was then bubbled through the solution for 0.5 hour, 49 mg of sodium borohydride were added in one portion and the mixture was left to stand at room temperature overnight. The solvent was removed by evaporation and the residue was partitioned between ethyl acetate and dilute hydrochloric acid. The organic phase was dried over sodium sulphate and evaporated, and the residue was recrystalized from acetic acid the give 20 mg of 7-[3-cyano-4-(2-hydroxyethoxy)phenyl]isothiazolo[4,5-d]-1,2,3-triazin-4(3H)-one as a white solid of melting point 190°-193° C. (dec.).

EXAMPLE 9

A solution of 500 mg of 7-(4-allyloxy-3-cyanophenyl)isothiazolo[4,5-d]-1,2,3-triazin-4(3H)-one and 200 mg of N-methylmorpholine N-oxide in 15 ml of dimethylformamide and 5 ml of water was treated with 1.75 ml of a 0.4% solution of osmium tetroxide in water. The mixture was stirred at room temperature for 7 days and then a solution of 220 mg of sodium dithionite in 5 ml of water was added. The solvent was removed by evaporation and the residue was extracted with hot ethyl acetate, filtered and the filtrate was evaporated. Recrystallization of the residue from acetic acid yielded 160 mg of 7-[3-cyano-4-(2,3-dihydroxypropoxy)phenyl]isothiazolo[4,5-d]-1,2,3-triazin-4(3H)-one as a white solid of melting point 195° C. (dec.).

EXAMPLE 10

562 mg of 3-amino-2-(3-trifluoromethylphenyl)-4-pyridinecarboxamide were stirred at 0° C. in 5 ml of concentrated hydrochloric acid during the addition of 160 mg of sodium nitrite in 1 ml of water. After 0.5 hour the mixture was diluted with water and ethyl acetate and made basic with sodium bicarbonate. The organic phase was separated, dried over sodium sulphate and evaporated, and the residue was purified by chromatography on silica gel using ethyl acetate/petroleum ether (1:1) for the elution. There were obtained 400 mg of 8-(3-trifluoromethylphenyl)pyrido[3,4-d]-1,2,3-triazin-4(3H)-one in the form of a solid of melting point 192°-193° C. (dec.).

EXAMPLE 11

639 mg of 3-amino-2-phenyl-4-pyridinecarboxamide in 7 ml of concentrated hydrochloric acid were stirred in an ice-bath during the addition of 240 mg of sodium nitrite in 2 ml of water. After 0.5 hour aqueous sodium bicarbonate solution was added until the mixture was basic and the produce was then extracted into ethyl acetate. The ethyl acetate extract was dried over sodium sulphate and evaporated, and the residue was recrystallized from ethanol to yield 420 mg of 8-phenyl-pyrido[3,4-d]-1,2,3-triazin-4(3H)-one of melting point 211° C. (dec.)

The 3-amino-2-phenyl-4-pyridinecarboxamide used as the starting material was prepared as follows:

1 g of 3-amino-2-phenyl-4-pyridinecarbonitrile was heated to reflux for 3.5 hours in 20 ml of water and 10 ml of dioxan in the presence of 4 g of Amberlite IRA-400-OH (basic form). The resin was removed by filtration and the filtrate was evaporated. The residue was chromatographed on silica gel using methanol/ethyl acetate (1:19) for the elution and the product was recrystallized from ethyl acetate/petroleum ether to yield 900 mg of 3-amino-2-phenyl-4-pyridinecarboxamide of melting point 163°–164° C.

The following pyridinecarboxamide starting materials were prepared in an analogous manner:
3-Amino-2-(3-fluoro-4-methoxyphenyl)-4-pyridinecarboxamide, m.p. 193°–195° C.;
3-amino-2-(3-chloro-4-methoxyphenyl)-4-pyridinecarboxamide, m.p. 213°–215° C.;
3-amino-2-(4-methoxy-3-trifluoromethylphenyl)-4-pyridinecarboxamide, m.p. 195°–197° C.; and
3-amino-2-(4-benzyloxy-3-trifluoromethylphenyl)-4-pyridinecarboxamide, m.p. 155°–157° C.

EXAMPLE 12

300 mg of 3-amino-2-(4-methoxyphenyl)-4-pyridinecarboxamide were stirred at 0° C. in 5 ml of glacial acetic acid and 1 ml of concentrated hydrochloric acid during the addition of 128 mg of sodium nitrite in 2 ml of water. The cooling bath was removed, 3 ml of water were added, the mixture was stirred for 0.5 hour and the precipitated product was removed by filtration. Recrystallization from aqueous dimethylformamide yielded 275 mg of 8-(4-methoxyphenyl)pyrido[3,4-d]-1,2,3-triazin-4(3H)-one as yellow needles of melting point 226° C. (dec.).

The following compounds were prepared in an analogous manner:
8-(4-Benzyloxyphenyl)pyrido[3,4-d]-1,2,3-triazin-4(3H)-one, m.p. 221° C. (dec.)
8-(3-fluoro-4-methoxyphenyl)pyrido[3,4-d]-1,2,3-triazin-4(3H)-one, m.p. 228°–230° C. (dec);
8-(3-chloro-4-methoxyphenyl)pyrido[3,4-d]-1,2,3-triazin-4(3H)-one, m.p. 235°–237° C. (dec.);
8-(4-methoxy-3-trifluoromethylphenyl)pyrido[3,4-d]-1,2,3-triazin-4(3H)-one, m.p. 233°–235° C. (dec.); and
8-(4-benzyloxy-3-trifluoromethylphenyl)pyrido[3,4-d]-1,2,3-triazin-4(3H)-one, m.p. 203°–205° C. (dec.).

The 3-amino-2-(4-methoxyphenyl)-4-pyridinecarboxamide used as the starting material in the first paragraph of this Example was prepared as follows:

1 g of 3-amino-2-(4-methoxyphenyl)-4-pyridinecarbonitrile was heated to reflux for 2 hours in 10 ml of water and 10 ml of dioxan in the presence of 4 g of Dowex 1X4-100 (OH form). The resin was removed by filtration and the filtrate was evaporated in order to remove dioxan. The aqueous residue was extracted with ethyl acetate and the organic phase was washed with water and sodium chloride solution, dried over sodium sulphate and evaporated. Recrystallization of the residue from ethyl acetate/hexane yielded 500 mg of 3-amino-2-(4-methoxyphenyl)-4-pyridinecarboxamide as a yellow solid of melting point 179°–181° C.

The following pyridinecarboxamide starting material was prepared in an analogous manner:
3-Amino-2-(4-benzyloxyphenyl)-4-pyridinecarboxamide, m.p. 201°–202° C.

EXAMPLE 13

500 mg of 1-(4-methoxyphenyl)-5-amino-4-pyrazolecarboxamide in 9 ml of glacial acetic acid and 5 ml of concentrated hydrochloric acid was stirred at 0° C. during the addition of a solution of 150 mg of sodium nitrite in 3 ml of water. The mixture was held at 0° C. for 10 minutes, then allowed to warm to room temperature and stirred for a further 20 minutes. The precipitated product was filtered off and recrystallized from aqueous dimethylformamide. There were obtained 150 mg of 7-(4-methexyphenyl)-7H-pyrazolo[3,4-d]-1,2,3-triazin-4(3H)-one of melting point 158°–160° C.

The 1-(4-methoxyphenyl)-5-amino-4-pyrazolecarboxamide used as the starting material was prepared as follows:

1.5 g of 1-(4-methoxyphenyl)-5-amino-4-pyrazolecarbonitrile were stirred at 10°–15° C. with 10 ml of concentrated sulphuric acid until all of the solid had dissolved. The mixture was poured on to 60 g of crushed ice and made basic with concentrated ammonia solution. The precipitated product was filtered off, washed with water and recrystallized from ethanol to give 900 mg of 1-(4-methoxyphenyl)-5-amino-4-pyrazolecarboxamide of melting point 213°–215° C.

EXAMPLE 14

1 g of 5-amino-1-phenyl-4-pyrazolecarboxamide in 18 ml of glacial acetic acid and 10 ml of concentrated hydrochloric acid was stirred at 0° C. during the addition of a solution of 0.4 g of sodium nitrite in 6 ml of water. The mixture was held at 0° C. for 20 minutes, then allowed to warm to room temperature and stirred for a further 2 hours. The precipitated product was filtered off and recrystallized from ethanol to yield 580 mg of 7-phenyl-7H-pyrazolo[3,4-d]-1,2,3-triazin-4(3H)-one of melting point 150°–151° C.

The 5-amino-1-phenyl-4-pyrazolecarboxamide used as the starting material was prepared as follows:

9 g of 5-amino-1-phenyl-4-pyrazolecarbonitrile were stirred at 10°–15° C. with 40 ml of concentrated sulphuric acid until all of the solid had dissolved. The mixture was poured on to 150 g of crushed ice and made basic with concentrated ammonia solution. The precipitated product was filtered off and purified by chromatography on silica gel using 5% methanol in ethyl acetate for the elution. There were obtained 5.8 g of 5-amino-1-phenyl-4-pyrazolecarboxamide. A sample recrystallized from water melted at 163°–165° C.

EXAMPLE 15

The following compounds were prepared in a manner analogous to that described in Examples 13 and 14:
7-(3-Trifluoromethylphenyl)-7H-pyrazolo[3,4-d]-1,2,3-triazin-4(3H)-one, m.p: 144°–145° C.;
7-(3-chlorophenyl)-7H-pyrazolo[3,4-d]-1,2,3-triazin-4(3H)-one, m.p. 153°–154° C.;

7-(4-ethylphenyl)-7H-pyrazolo[3,4-d]-1,2,3-triazin-4(3H)-one, m.p. 135°–136° C.;

7-(4-methylthiophenyl)-7H-pyrazolo[3,4-d]-1,2,3-triazin-4(3H)-one, m.p. 150°–152° C.; and 7-(3-chloro-4-methoxyphenyl)-7H-pyrazolo[3,4-d]-1,2,3-triazin-4(3H)-one, m.p. 161°–163° C. (dec.).

The following Examples illustrate pharmaceutical preparations containing the compounds provided by the present invention:

EXAMPLE A

Tablets containing the following ingredients may be produced in a conventional manner:

| Ingredient | Per tablet |
|---|---|
| 7-(3-Trifluoromethyl-4-methoxyphenyl)-isothiazolo[4,5-d]-1,2,3-triazin-4(3H)-one | 5 mg |
| Lactose | 125 mg |
| Maize starch | 65 mg |
| Talc | 4 mg |
| Magnesium stearate | 1 mg |
| Tablet weight | 200 mg |

EXAMPLE B

Capsules containing the following ingredients may be produced in a conventional manner:

| Ingredient | Per capsule |
|---|---|
| 7-(3-Chloro-4-methoxyphenyl)isothiazolo-[4,5-d]-1,2,3-triazin-4(3H)-one | 10 mg |
| Lactose | 165 mg |
| Maize starch | 20 mg |
| Talc | 5 mg |
| Capsule fill weight | 200 mg |

We claim:

1. A compound of the formula

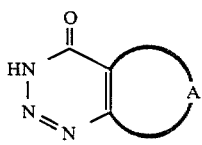

I wherein A is a grouping of the formula

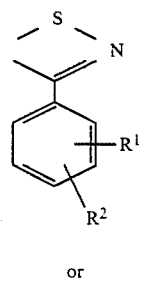

(a)

or

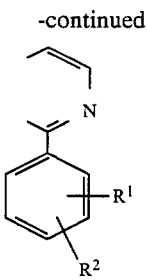

(b)

in which each of $R^1$ and $R^2$ individually is hydrogen, halogen, trifluoromethyl, nitro, amino, cyano, $C_1$–$C_6$-alkyl, $C_1$–$C_6$-alkoxy, $C_3$–$C_6$-alkenyloxy, $C_1$–$C_6$-alkylthio, $C_1$–$C_6$-alkanoylamino, aryloxy, aryl-($C_1$–$C_6$-alkyl), aryl-($C_1$–$C_6$-alkoxy), aryl-($C_1$–$C_6$-alkoxy)carbonylamino or —O—$CH_2$—$R^3$ or $R^1$ and $R^2$ on adjacent carbon atoms together are —CH=CH—CH=CH— or —$CH_2$—$CH_2$—O—, and $R^3$ is hydroxy-($C_1$–$C_4$-alkyl) or vicinal dihydroxy-($C_2$–$C_3$-alkyl), said aryl moiety in the above substituents being unsubstituted phenyl or phenyl substituted with at least one substituent selected from the group consisting of halogen, trifluoromethyl, $C_1$–$C_6$-alkyl, $C_1$–$C_6$-alkoxy, nitro and cyano, and pharmaceutically acceptable acid addition salts of those compounds of formula I in which at least one of $R^1$ and $R^2$ is amino, or tautomers thereof.

2. The compound of claim 1, in which $R^1$ and $R^2$ each individually is hydrogen, halogen, trifluoromethyl, nitro, amino, cyano, $C_1$–$C_6$-alkyl, $C_1$–$C_6$-alkoxy, $C_1$–$C_6$-alkylthio, $C_1$–$C_6$-alkanoylamino, aryloxy, aryl-($C_1$–$C_6$-alkyl), aryl-($C_1$–$C_6$-alkoxy) or aryl-($C_1$–$C_6$-alkoxy)carbonylamino, or $R^1$ and $R^2$ on adjacent carbon atoms together are —CH=CH—CH=CH— or —$CH_2$—$CH_2$—O—.

3. The compound of claim 1, wherein A is a grouping of formula (a).

4. The compound of claim 3, wherein $R^1$ is hydrogen, halogen, trifluoromethyl or cyano and $R^2$ is hydrogen, $C_1$–$C_6$-alkoxy, aryl-($C_1$–$C_6$-alkoxy) or —O—$CH_2$—$R^3$ in which $R^3$ is vicinal dihydroxy-($C_2$–$C_5$-alkyl), with the proviso that at least one of $R^1$ and $R^2$ is other than hydrogen.

5. The compound of claim 3, 7-(3-trifluoromethyl-4methoxyphenyl)isothiazolo[4,5-d]-1,2,3-triazin-4(3H)-one.

6. The compound of claim 3, 7-(3-chloro-4-methoxyphenyl) isothiazolo[4,5-d]-1,2,3-triazin-4(3H)-one.

7. The compound of claim 3, 7-(3-fluoro-4-methoxyphenyl) isothiazolo[4,5-d]-1,2,3-triazin-4(3H)-one.

8. The compound of claim 3, 7-(3-trifluoromethylphenyl) isothiazolo[4,5-d]-1,2,3-triazin-4(3H)-one.

9. The compound of claim 3,7-(4-isopropoxyphenyl) isothiazolo[4,5-d]-1,2,3-triazin-4(3H)-one.

10. The compound of claim 3,7((4-benzyloxyphenyl) isothiazolo[4,5-d]-1,2,3-triazin-4(3H)-one.

11. The compound of claim 3,7-(3-cyano-4-methoxyphenyl) isothiazolo[4,5-d]-1,2,3-triazin-4(3H)-one.

12. The compound of claim 3,7-[3-cyano-4-(2,3-dihydroxypropoxy)phenyl]isothiazolo-[4,5-d]-1,2,3-triazin-4(3H)-one.

13. The compound of claim 2, selected from the group consisting of:
7-Phenylisothiazolo[4,5-d]-1,2,3-triazin-4(3H)-one,
7-(3-ethylphenyl)isothiazolo[4,5-d]-1,2,3-triazin-4(3H)-one, 7-(3-methylphenyl)isothiazolo[4,5-d]-1,2,3-triazin-4(3H)-one,
7-(3-chlorophenyl)isothiazolo[4,5-d]-1,2,3-triazin-4(3H)-one,
7-(3-bromophenyl)isothiazolo[4,5-d]-1,2,3-triazin-4(3H)-one,
7-(3-cyanophenyl)isothiazolo[4,5-d]-1,2,3-triazin-4(3H)-one,
7-(3-methoxyphenyl)isothiazolo[4,5-d]-1,2,3-triazin-4(3H)-one,
7-(4-methoxyphenyl)isothiazolo[4,5-d]-1,2,3-triazin-4(3H)-one,
7-(3-fluorophenyl)isothiazolo[4,5-d]-1,2,3-triazin-4(3H)-one,
7-(4-acetamidophenyl)isothiazolo[4,5-d]-1,2,3-triazin-4(3H)-one,
7-(4-benzyloxyformamidophenyl)isothiazolo[4,5-d]-1,2,3-triazin-4(3H)-one,
7-(4-aminophenyl)isothiazolo[4,5-d]-1,2,3-triazin-4(3H)-one,
7-(4-nitrophenyl)isothiazolo[4,5-d]-1,2,3-triazin-4(3H)-one,
7-(4-chlorophenyl)isothiazolo[4,5-d]-1,2,3-triazin-4(3H)-one,
7-(4-bromophenyl)isothiazolo[4,5-d]-1,2,3-triazin-4(3H)-one,
7-(4-phenoxyphenyl)isothiazolo[4,5-d]-1,2,3-triazin-4(3H)-one,
7-(2-naphthyl)isothiazolo[4,5-d]-1,2,3-triazin-4(3H)-one,
7-(2,3-dihydro-5-benzofuranyl)isothiazolo[4,5-d]-1,2,3-triazin-4(3H)-one,
7-(3,5-dimethylphenyl)isothiazolo[4,5-d]-1,2,3-triazin-4(3H)-one,
7-(4-benzylphenyl)isothiazolo[4,5-d]-1,2,3-triazin-4(3H)-one,
7-(3-isopropylphenyl)isothiazolo[4,5-d]-1,2,3-triazin-4(3H)-one,
7-[3,5-bis(trifluoromethyl)phenyl]isothiazolo[4,5-d]-1,2,3-triazin-4(3H)-one,
7-(3-trifluoromethyl-4-benzyloxyphenyl)isothiazolo[4,5-d]-1,2,3-triazin-4(3H)-one,
8-phenylpyrido[3,4-d]-1,2,3-triazin-4(3H)-one, and
8-(3-trifluoromethylphenyl)pyrido[3,4-d]-1,2,3-triazin-4-(3H)-one.

14. The compound of claim 1, selected from the group consisting of:
7-(4-Ethylphenyl)isothiazolo[4,5-d]-1,2,3-triazin-4(3H)-one,
7-(4-isobutylphenyl)isothiazolo[4,5-d]-1,2,3-triazin-4(3H)-one,
7-(4-allyloxy-3-cyanophenyl)isothiazolo[4,5-d]-1,2,3-triazin-4(3H)-one,
7-[3-cyano-4-(2-hydroxyethoxy)phenyl]isothiazolo[4,5-d-1,2,3-triazin-4(3H)-one,
7-[3-cyano-4-(3-hydroxypropoxy)phenyl]isothiazolo[4,5-d]-1,2,3-triazin-4-(3H)-one,
7-[3-cyano-4-methylthiophenyl]isothiazolo[4,5-d]-1,2,3-triazin-4(3H)-one,
8-(4-methoxyphenyl)pyrido[3,4-d]-1,2,3-triazin-4(3H)-one,
8(4-benzyloxyphenyl)pyrido[3,4-d]-1,2,3-triazin-4(3H)-one,
8-(3-fluoro-4-methoxyphenyl)pyrido[3,4-d]-1,2,3-triazin-4(3H)-one,
8-(3-chloro-4-methoxyphenyl)pyrido[3,4-d]-1,2,3-triazin-4(3H)-one,
8-(4-methoxy-3-trifluoromethylphenyl)pyrido[3,4-d]-1,2,3-triazin-4(3H)-one, and
8-(4-benzyloxy-3-trifluoromethylphenyl)pyrido[3,4-d]-1,2,3-triazin-4(3H)-one.

15. A compound of the formula

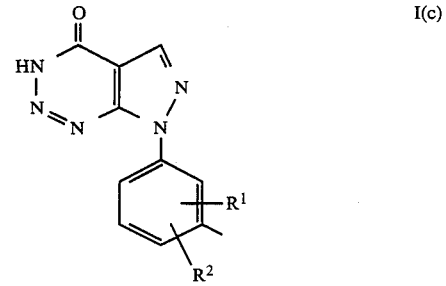

I(c)

wherein each of $R^1$ and $R^2$ individually is hydrogen, halogen, trifluoromethyl, nitro, amino, cyano, $C_1$-$C_6$-alkyl, $C_1$-$C_6$-alkoxy, $C_3$-$C_6$-alkenyloxy, $C_1$-$C_6$-alkylthio, $C_1$-$C_6$-alkanoylamino, aryloxy, aryl-($C_1$-$C_6$-alkyl), aryl-($C_1$-$C_6$-alkoxy), aryl-($C_1$-$C_6$-alkoxy)carbonylamino or —O—$CH_2$—$R^3$, or $R^1$ and $R^2$ on adjacent carbon atoms together are —CH=CH—CH=CH— or —$CH_2$—$CH_2$—O—, and $R^3$ is hydroxy-($C_1$-$C_4$-alkyl) or vicinal dihydroxy-($C_2$-$C_5$-alkyl), said aryl moiety in the above substituents being unsubstituted phenyl or phenyl substituted with at least one substituent selected from the group consisting of halogen, trifluoromethyl, $C_1$-$C_6$-alkyl, $C_1$-$C_6$-alkoxy, nitro and cyano; with the proviso that when $R^1$ or $R^2$ is halogen, $C_1$-$C_6$-alkyl or $C_1$-$C_6$-alkoxy, the other of $R^1$ and $R^2$ is other than hydrogen; with the further proviso that when one of $R^1$ and $R^2$ is hydrogen the other of $R^1$ and $R^2$ is not hydrogen, and pharmaceutically acceptable acid addition salts of those compounds of formula I in which at least one of $R^1$ and $R^2$ is amino, or tautomers thereof.

16. The compound of claim 15, selected from the group consisting of:
7-(3-trifluoromethylphenyl)-7H-pyrazolo[3,4-d-]1,2,3-triazin-4(3H)-one,
7-(4-methylthiophenyl)-7H-pyrazolo[3,4-d]-1,2,3-triazin-4(3H)-one, and
7-(3-chloro-4-methoxyphenyl)-7H-pyrazolo[3,4-d]-1,2,3-triazin-4(3H)-one.

17. A method of treating ischemia or gout in an afflicted mammal comprising administering to the mammal a compound of the formula

I wherein A is a grouping of the formula

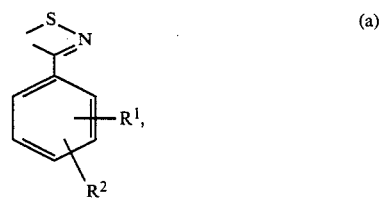

(a)

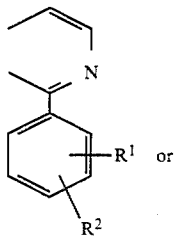 or

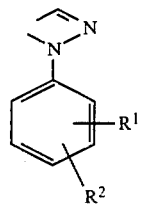

in which $R^1$ and $R^2$ each individually is hydrogen, halogen, trifluoromethyl, nitro amino, cyano, $C_1$-$C_6$-alkyl, $C_1$-$C_6$-alkoxy, $C_3$-$C_6$-alkenyloxy, $C_1$-$C_6$-alkylthio, $C_1$-$C_6$-alkanoylamino, aryloxy, aryl-($C_1$-$C_6$-alkyl), aryl-($C_1$-$C_6$-alkoxy), aryl-($C_1$-$C_6$-alkoxy)carbonylamino or —O—$CH_2$—$R^3$, or $R^1$ and $R^2$ on adjacent carbon atoms together are —CH=CH—CH=CH' or —$CH_2$—$CH_2$—O—, and $R^3$ is hydroxy-($C_1$-$C_4$-alkyl) or vicinal dihydroxy-($C_2$-$C_5$-alkyl), and pharmaceutically acceptable acid addition salts of those compounds of formula I in which at least one of $R^1$ and $R^2$ is amino, or tautomers thereof, in an amount which is effective in treating ischemia or gout.

* * * * *

UNITED STATES PATENT AND TRADEMARK OFFICE
CERTIFICATE OF CORRECTION

PATENT NO. : 4,920,119
DATED : April 24, 1990
INVENTOR(S) : Michael R. Attwood, Peter H. Crackett, Geoffrey Lawton It is certified that error appears in the above-identified patent and that said Letters Patent is hereby corrected as shown below:

Claim 1, column 16, line 21, "$(C_2-C_3-alkyl)$" should read -- $(C_2-C_5-alkyl)$ --.

Claim 5, column 16, line 47, "4methoxyphenyl" should read -- 4-methoxyphenyl --.

Claim 10, column 16, line 57 ,"3,7((4-benzyloxyphenyl)" should read -- 3,7-(4-benzyloxyphenyl) --.

Claim 17, column 20, line 17, "-CH=CH-CH=CH'" should read -- -CH=CH-CH=CH- --.

Signed and Sealed this

Twenty-eighth Day of May, 1991

Attest:

HARRY F. MANBECK, JR.

Attesting Officer

Commissioner of Patents and Trademarks